United States Patent
Kageyama et al.

(10) Patent No.: US 11,084,782 B2
(45) Date of Patent: Aug. 10, 2021

(54) GAS GENERATING AGENT, AND METHOD FOR PRODUCING FOAM USING THE SAME

(71) Applicants: Mitsubishi Gas Chemical Company, Inc., Tokyo (JP); Eiwa Chemical Ind. Co., Ltd., Kyoto (JP)

(72) Inventors: Takuya Kageyama, Tokyo (JP); Haruka Sakai, Tokyo (JP); Kazuyoshi Uera, Tokyo (JP); Tomoki Iwata, Tokyo (JP); Yuji Yasuda, Aichi (JP); Kazuya Nakata, Aichi (JP); Hiroshi Iwasaki, Aichi (JP); Mitsuru Kasuga, Aichi (JP)

(73) Assignees: Mitsubishi Gas Chemical Company, Inc., Tokyo (JP); Eiwa Chemical Ind. Co., Ltd., Kyoto (JP)

( * ) Notice: Subject to any disclaimer, the term of this patent is extended or adjusted under 35 U.S.C. 154(b) by 44 days.

(21) Appl. No.: 16/722,044

(22) Filed: Dec. 20, 2019

(65) Prior Publication Data
US 2020/0123101 A1    Apr. 23, 2020

Related U.S. Application Data

(62) Division of application No. 15/567,910, filed as application No. PCT/JP2016/061802 on Apr. 12, 2016, now abandoned.

(30) Foreign Application Priority Data

Apr. 23, 2015  (JP) .................. 2015-088657

(51) Int. Cl.
| | | |
|---|---|---|
| C07C 281/16 | (2006.01) | |
| C07C 55/07 | (2006.01) | |
| C08J 9/10 | (2006.01) | |
| C08K 5/31 | (2006.01) | |

(52) U.S. Cl.
CPC ............ *C07C 281/16* (2013.01); *C07C 55/07* (2013.01); *C08J 9/10* (2013.01); *C08J 9/104* (2013.01); *C08K 5/31* (2013.01); *C08J 2201/026* (2013.01); *C08J 2300/22* (2013.01); *C08J 2300/26* (2013.01); *C08J 2323/06* (2013.01); *C08J 2323/16* (2013.01)

(58) Field of Classification Search
CPC .......... C07C 281/16; C07C 55/07; C08J 9/10; C08J 9/104; C08K 5/31
See application file for complete search history.

(56) References Cited

U.S. PATENT DOCUMENTS

| | | | |
|---|---|---|---|
| 3,977,922 A | 8/1976 | Inoue et al. | |
| 6,468,369 B1 | 10/2002 | Zhou | |
| 6,515,055 B1 | 2/2003 | Nohara et al. | |
| 2008/0251169 A1* | 10/2008 | Nicolich | C07F 9/54 149/22 |
| 2012/0055631 A1* | 3/2012 | Finter | C08G 59/4246 156/330 |
| 2015/0191400 A1 | 7/2015 | Fujisaki et al. | |
| 2017/0121429 A1* | 5/2017 | Iwata | C08K 3/04 |

FOREIGN PATENT DOCUMENTS

| | | |
|---|---|---|
| CN | 102803424 A | 11/2012 |
| EP | 3156394 A1 | 4/2017 |
| GB | 1290418 A | 9/1972 |
| JP | S48-30673 B | 9/1973 |
| JP | H07-309194 A | 11/1995 |
| JP | H11-21364 A | 1/1999 |
| JP | H11-292678 A | 10/1999 |
| JP | H11-314992 A | 11/1999 |
| JP | 2001-139728 A | 5/2001 |
| JP | 3953187 B2 | 8/2007 |
| WO | 97/29927 A2 | 8/1997 |
| WO | 2014/061396 A1 | 4/2014 |
| WO | 2014/086599 A1 | 6/2014 |

OTHER PUBLICATIONS

Derwent abstract of JP 73030673. (Year: 1973).*
International Search Report for International Application No. PCT/JP2016/061802 dated Jul. 12, 2016, and English translation (5 pages).

* cited by examiner

*Primary Examiner* — Michael M Dollinger
*Assistant Examiner* — Christina H. W. Rosebach
(74) *Attorney, Agent, or Firm* — Fitch, Even, Tabin & Flannery, LLP

(57) ABSTRACT

The gas generating agent of the present invention comprises an oxalic acid salt of an aminoguanidine compound represented by general formula (1) below.

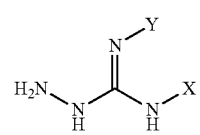

(1)

7 Claims, No Drawings

GAS GENERATING AGENT, AND METHOD FOR PRODUCING FOAM USING THE SAME

CROSS-REFERENCE TO RELATED APPLICATIONS

This application is a divisional of prior application Ser. No. 15/567,910, filed Oct. 19, 2017, which is a U.S. national phase application filed under 35 U.S.C. § 371 of International Application PCT/JP2016/061802, filed Apr. 12, 2016, designating the United States, which claims priority from Japanese Application Number 2015-088657, filed Apr. 23, 2015.

FIELD OF THE INVENTION

The present invention relates to a gas generating agent and a method for producing a foam of a thermoplastic resin, a rubber, or the like using the gas generating agent.

BACKGROUND OF THE INVENTION

Azodicarbonamide (hereinafter also referred to as "ADCA"), which is a typical gas generating agent, is a compound used in a broad range of applications as a chemical blowing agent for plastics and rubbers in general.

Advantages of ADCA include that the amount of generated gas is 200 mL/g or more and is larger than that of other commercially available chemical blowing agents, that the degradation starting temperature can be lowered to near 140° C. by using a blowing auxiliary in combination although the degradation starting temperature is relatively high at 200 to 210° C. so that ADCA is applicable to general-purpose plastics (for example, thermoplastic resins) and rubbers, and that the generated gas is mainly composed of nitrogen and is self-extinguishing so that ADCA is highly safe in terms of handling.

On the other hand, ADCA has problems in that a small amount of ammonia gas is contained in the gas generated during foaming and this ammonia gas is corrosive, and that cyanic acid, which is a degradation product of ADCA, is sublimable and polymerizes after sublimation to become corrosive cyanuric acid, which is likely to cause metal mold contamination (see, for example, Patent Literature 1 and Non Patent Literature 1).

In the fields that do not welcome such disadvantages of ADCA, i.e., ammonia and contaminating characteristics, 4,4'-oxybis(benzenesulfonyl hydrazide) (hereinafter also referred to as "OBSH") is used as a gas generating agent, the generated gases of which are only nitrogen and water and also the degradation product of which is not contaminating. OBSH has a low degradation starting temperature of about 170° C. and is mainly used for ethylene-propylene-diene rubber (EPDM) for weather strips and chloroprene rubber (CR) for wet suits.

However, OBSH is problematic from the viewpoint of economy and resource saving because the amount of generated gas is as small as 120 mL/g and it is necessary to increase the amount of OBSH added to obtain a desired expansion ratio.

In addition to ADCA and OBSH, guanidine derivatives such as guanidine salts, aminoguanidine salts, diaminoguanidine salts, and triaminoguanidine salts can also be used as gas generating agents. These guanidine derivatives are also used for antioxidants for explosives, pharmaceuticals, and fiber processing, soap resin stabilizers, and other various synthetic raw materials (see, for example, Non Patent Literature 2). Specifically, for example, gas generating agents containing carbonic acid salts, nitric acid salts, and perchloric acid salts of guanidine derivatives are disclosed for air bag systems (see, for example, Patent Literatures 2 to 4).

CITATION LIST

Patent Literature

Patent Literature 1: Japanese Patent Laid-Open No. 11-21364
Patent Literature 2: International Publication No. WO 97/29927
Patent Literature 3: Japanese Patent Laid-Open No. 11-292678
Patent Literature 4: Japanese Patent No. 3953187

Non Patent Literature

Non Patent Literature 1: Hitoshi Kondo, "The Characteristic of Foaming Agents", Nippon Gomu Kyokaishi, The Society of Rubber Science and Technology, Japan, 2001, Vol. 74, No. 10, pp. 406-411
Non Patent Literature 2: "Guanidine Salts", Fine Chemical, CMC Publishing Co., Ltd., June 2008, Vol. 37, No. 6, pp. 72-75

SUMMARY OF INVENTION

However, although the above nitric acid salts and the like of guanidine derivatives are easily synthesized and are widely used compounds, the amount of generated gas is small when such a compound is used singly. The above carbonic acid salts of guanidine derivatives have a degradation starting temperature of lower than 100° C., which is greatly different from the molding temperatures of general-purpose plastics (for example, thermoplastic resins) and rubbers. Thus, it is difficult to use the above conventional nitric acid salts and carbonic acid salts of guanidine derivatives as gas generating agents intended for chemical blowing agents for general-purpose plastics (for example, thermoplastic resins) and rubbers unlike ADCA and OBSH.

Accordingly, an object of the present invention is to provide a gas generating agent which, for example, has a degradation starting temperature at which the gas generating agent is usable as a chemical blowing agent for general-purpose plastics (for example, thermoplastic resins) and rubbers, generates a large amount of gas, and barely contains corrosive gas such as ammonia in the generated gas using an easily synthesized and widely used guanidine derivative.

As a result of diligent research, the inventors found that a compound which is a salt formed from an aminoguanidine compound represented by a specific chemical formula and oxalic acid solves the above problems, and the inventors accomplished the present invention.

That is to say, the present invention is as follows.

[1]

A gas generating agent comprising an oxalic acid salt of an aminoguanidine compound represented by general formula (1) below.

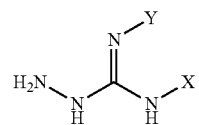
(1)

(In the formula, X and Y are each independently a hydrogen atom or an amino group.)

[2]

The gas generating agent according to [1], wherein in the oxalic acid salt of the aminoguanidine compound, a molar ratio of the aminoguanidine compound to oxalic acid (aminoguanidine compound:oxalic acid) is in a range of 1:1 to 2:1.

[3]

The gas generating agent according to [1] or [2], wherein the aminoguanidine compound is aminoguanidine.

[4]

The gas generating agent according to any of [1] to [3], wherein the gas generating agent is a microcapsule-based agent.

[5]

A foamable composition comprising the gas generating agent according to any of [1] to [4] and a material to be foamed.

[6]

The foamable composition according to [5], wherein the material to be foamed is a thermoplastic resin and/or a rubber.

[7]

A method for producing a foam, comprising a step of heating the foamable composition according to [5] or [6].

[8]

A foam, wherein the foam obtained by foaming the foamable composition according to [5] or [6].

The present invention can provide a gas generating agent which, for example, has a degradation starting temperature at which the gas generating agent is usable as a chemical blowing agent for general-purpose plastics (for example, thermoplastic resins) and rubbers, generates a large amount of gas, and barely contains corrosive gas such as ammonia in the generated gas using an easily synthesized and widely used chemical raw material guanidine derivative and oxalic acid.

DESCRIPTION OF EMBODIMENT

Below, an embodiment (hereinafter also referred to as "the present embodiment") of the present invention is described in detail. The following embodiment is an example for describing the present invention, and the present invention is not limited only to the embodiment. The gas generating agent of the present embodiment comprises an oxalic acid salt of an aminoguanidine compound represented by general formula (1) below (hereinafter also simply referred to as an "aminoguanidine compound").

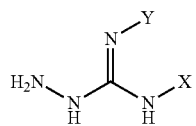
(1)

(In the formula, X and Y are each independently a hydrogen atom or an amino group.)

In the gas generating agent of the present embodiment, oxalic acid is used for the acid that forms a salt with an aminoguanidine compound. The use of an oxalic acid salt of an aminoguanidine compound such as aminoguanidine makes it possible to obtain a gas generating agent that has a degradation starting temperature at which the gas generating agent is usable as a chemical blowing agent for general-purpose plastics (for example, thermoplastic resins) and rubbers, generates a large amount of gas, and barely contains corrosive gas such as ammonia in the generated gas.

The amount of generated gas during the foaming of the gas generating agent of the present embodiment is preferably 120 mL/g or more.

The amount of generated ammonia during the foaming of the gas generating agent of the present embodiment is preferably 10 mg/g or less, more preferably 5 mg/g or less, and even more preferably 1 mg/g.

The degradation starting temperature of the gas generating agent of the present embodiment is preferably a degradation starting temperature at which the gas generating agent is usable as a chemical blowing agent for, for example, general-purpose plastics (for example, thermoplastic resins) and rubbers and, specifically, is preferably 90 to 380° C. and more preferably 110 to 250° C.

In the present embodiment, the amount of generated gas during foaming, the amount of generated ammonia, and the degradation starting temperature of the gas generating agent can be measured by the methods described in the Examples below.

The oxalic acid salt of an aminoguanidine compound used in the present embodiment is obtained by reacting an aminoguanidine compound and oxalic acid. The aminoguanidine compound is not particularly limited, and examples include aminoguanidine, diaminoguanidine, and triaminoguanidine. In particular, aminoguanidine is preferable. Oxalic acid used in the above reaction is a known compound and can be obtained as a commercially available product, and both anhydrated oxalic acid and oxalic acid dihydrate are usable.

Although an aminoguanidine compound not forming a salt can also be used as the aminoguanidine compound used in the above reaction, it is preferable to use a salt of an aminoguanidine compound because an aminoguanidine compound has enhanced stability and also becomes easily obtainable when it is in the form of a salt with an acid. The acid that forms a salt with an aminoguanidine compound is not particularly limited, and examples include hydrochloric acid, sulfuric acid, phosphoric acid, sulfamic acid, nitric acid, perchloric acid, carbonic acid, hydroiodic acid, hydrobromic acid, and thiocyanic acid. Among these acids, acids that have a lower acidity than oxalic acid are preferable because the use, as a raw material, of an aminoguanidine compound forming a salt with such an acid facilitates synthesis. Such salts of an aminoguanidine compound include aminoguanidine carbonate and the like.

Next, described are the reaction conditions for obtaining the oxalic acid salt of an aminoguanidine compound used in the gas generating agent of the present embodiment from the carbonic acid salt of an aminoguanidine compound and oxalic acid. The reaction progresses by using 1 mol to an excess of oxalic acid per mole of the carbonic acid salt of an aminoguanidine compound, and performing stirring in a polar solvent such as water or alcohol under normal pressure at 0 to 100° C. for 10 minutes to 24 hours for reaction. After reaction, the target product is purified by a known method. An example of a method is cooling with ice water or the like to precipitate and isolate crystals to obtain crude crystals.

The proportion of the carbonic acid salt of an aminoguanidine compound and oxalic acid used is preferably 1:1 to 1:100 and more preferably 1:1 to 1:10 as a molar ratio (carbonic acid salt:oxalic acid). The reaction may be performed at room temperature or may be performed with increasing temperature as necessary, and in consideration of the boiling point of the polar solvent such as water or alcohol, the reaction is preferably performed at 0 to 100° C. and more preferably 20 to 80° C.

The above polar solvent is not particularly limited, examples include water, methanol, ethanol, propanol, isopropyl alcohol, butanol, and isobutyl alcohol, and water is preferable with which the purification of the product is easy and which is highly economical.

After the end of reaction, crystals precipitated by a cooling operation or the like are filtered off, washed with water, alcohol, or the like, and dried under reduced pressure, and thus the oxalic acid salt of an aminoguanidine compound can be obtained.

While the oxalic acid salt of an aminoguanidine compound used in the present embodiment usually forms a salt in a proportion of the aminoguanidine compound:oxalic acid=1:1, it may form a salt in a proportion of the aminoguanidine compound:oxalic acid=2:1, and it may be a mixture of both of these. In the oxalic acid salt of an aminoguanidine compound used in the present embodiment, the molar ratio of the aminoguanidine compound to oxalic acid (aminoguanidine compound:oxalic acid) is preferably in a range of 1:1 to 2:1, more preferably in a range of 1:1 to 1.5:1, and even more preferably in a range of 1:1 to 1.2:1.

Accordingly, the oxalic acid salt of an aminoguanidine compound used in the present embodiment can also be represented by, for example, formula (1-1) below.

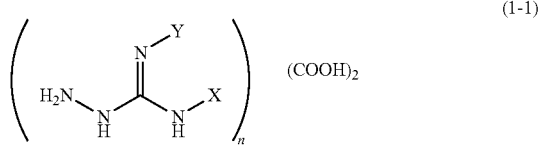

(1-1)

(In the formula, X and Y are each independently a hydrogen atom or an amino group, and n is a number in a range of 1.0 to 2.0.)

The oxalic acid salt of an aminoguanidine compound obtained as described above can be used as a gas generating agent. The gas generating agent of the present embodiment can be suitably used as, for example, a chemical blowing agent for general-purpose plastics (for example, thermoplastic resins) and rubbers. The oxalic acid salt of an aminoguanidine compound used for the gas generating agent of the present embodiment can suppress the generation of corrosive gas such as ammonia and provide a foam having a high expansion ratio when used alone at the foam molding temperature (for example, about 130 to 250° C.) of general-purpose plastics (for example, thermoplastic resins) and rubbers.

Although the gas generating agent of the present embodiment can be suitably used as a chemical blowing agent for general-purpose plastics (for example, thermoplastic resins) and rubbers even when composed solely of the oxalic acid salt of an aminoguanidine compound, the gas generating agent may further comprise an adjuvant in addition to the oxalic acid salt of an aminoguanidine compound. The adjuvant is not particularly limited, and examples include oxidizers, crosslinking agents (C), nitrous acid salts, and hydrotalcite. When the gas generating agent of the present embodiment further comprises such an adjuvant, there is a tendency that the generation of corrosive gas such as ammonia can be further suppressed, and the temperature when producing a foam, which will be described below, also is in a suitable range.

When an adjuvant in addition to the oxalic acid salt of an aminoguanidine compound is contained in the gas generating agent of the present embodiment, the content of the oxalic acid salt of an aminoguanidine compound is preferably 0.5 to 95 mass % based on the total mass of the oxalic acid salt of an aminoguanidine compound and the adjuvant.

The oxidizers are not particularly limited, and an example is sodium percarbonate. One oxidizer may be used singly, or two or more may be used in combination.

In the gas generating agent of the present embodiment, the content of the oxidizer is preferably 0.5 to 95 mass % and more preferably 5 to 50 mass % based on the total mass of an oxalic acid salt of an aminoguanidine compound and the adjuvant.

The crosslinking agents (C) are not particularly limited, and examples include dicumyl peroxide, di-t-butyl peroxide, 2,5-dimethyl-2,5-di-(t-butylperoxy)hexane, 2,5-dimethyl-2,5-di-(t-butylperoxy)hexyne, 1,3-bis(t-butylperoxyisopropyl)benzene, 1,1-bis(t-butylperoxy)-3,3,5-trimethylcyclohexane, 1,1-bis[t-butylperoxy]cyclohexane, n-butyl-4,4-bis(t-butylperoxy)valerate, benzoyl peroxide, p-chlorobenzoyl peroxide, 2,4-dichlorobenzoyl peroxide, t-butyl peroxybenzoate, t-butyl perbenzoate, t-butylperoxy isopropyl carbonate, diacetyl peroxide, lauroyl peroxide, and t-butyl cumyl peroxide. One crosslinking agent (C) may be used singly, or two or more may be used in combination.

In the gas generating agent of the present embodiment, the content of the crosslinking agent (C) is preferably 0.1 to 10 mass % and more preferably 0.5 to 1.5 mass % based on the total mass of an oxalic acid salt of an aminoguanidine compound and the adjuvant. The nitrous acid salts are not particularly limited, and examples include sodium nitrite, potassium nitrite, and calcium nitrite. One selected from these can be used singly, or two or more can be used in combination. These nitrous acid salts preferably are pulverized fine powder.

In the gas generating agent of the present embodiment, the content of a nitrous acid salt is preferably 0.5 to 60 mass % and more preferably 15 to 55 mass % based on the total mass of an oxalic acid salt of an aminoguanidine compound and the adjuvant.

The hydrotalcite is a crystalline composite metal hydroxide, and hydrotalcite represented by general formula (H) below is preferable.

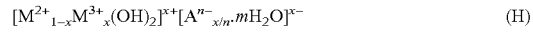

(H)

In general formula (H) above, $M^{2+}$ is a divalent metal ion of a metal selected from the group consisting of Mg, Mn, Fe, and Zn, $M^{3+}$ is a trivalent metal ion of a metal selected from the group consisting of Al, Fe, and Cr, $A^{n-}$ is an anion having a valency of n selected from the group consisting of OH, F, Cl, Br, $NO_3$, $CO_3$, and $SO_4$, x is in a range of $0<x\leq0.33$, n is an integer, and m is 0 or greater.

Here, m is preferably 0 but varies depending of the dryness and the state of storage of hydrotalcite, and thus m is not particularly limited as long as the effect of the present invention is not impaired. And, n is the valency of an anion and is preferably 1 or 2 and more preferably 2.

Among these, hydrotalcite in which $M^{2+}$ is $Mg^{2+}$ and $M^{3+}$ is $Al^{3+}$ is preferable, and the molar ratio of Al:Mg is preferably 2:5 to 2:10 in terms of availability. For example, when the molar ratio of Al:Mg is 2:5, the molar fraction x of Al (x=Al/(Mg+Al)) is 0.29, and when the molar ratio of Al to Mg is 2:10, the molar fraction x of Al is 0.17.

The hydrotalcite acts to enhance the reactivity of a nitrous acid salt. Blending hydrotalcite makes it possible to promote the degradation of ammonia gas that may be generated when heating the gas generating agent, enhance the reactivity of a nitrous acid salt to thereby suppress the generation of nitrous acid gas, and promote the generation of nitrogen gas to enhance the foamability of the gas generating agent. Although the particle diameter of the hydrotalcite is not particularly limited, increased dispersibility in the gas generating agent is preferable for causing hydrotalcite to effectively act on the reaction between an oxalic acid salt of an aminoguanidine compound and a nitrous acid salt, and fine-powder hydrotalcite having a maximum particle diameter of 80 μm or less is more preferable.

In the gas generating agent of the present embodiment, the content of the hydrotalcite is preferably 1 to 40 mass % and more preferably 5 to 25 mass % based on the total mass of the oxalic acid salt of the aminoguanidine compound and the adjuvant.

Various stabilizers, pigments/fillers, foaming regulators, and the like may be further blended with the gas generating agent of the present embodiment as long as the effect of the present invention is not impaired. Stabilizers are not particularly limited, and examples include tribasic lead sulphate, dibasic phosphorous acid salts, lead stearate, zinc stearate, zinc carbonate, zinc oxide, aluminum stearate, dibutyltin malate, and urea. Examples of pigments/fillers are not particularly limited, and examples include chrome yellow, carbon black, titanium dioxide, and calcium carbonate. Foaming regulators are not particularly limited, and examples include maleic acid and the like.

A method for producing the gas generating agent of the present embodiment is not particularly limited, and a commonly used mixing method can be used. For example, an oxalic acid salt of an aminoguanidine compound, a nitrous acid salt, and hydrotalcite may be mixed to be uniformly dispersed under conditions including a temperature of 60° C. or less and a time of about 5 minutes using a high speed mixer, a ribbon blender, a cone blender, or the like.

The gas generating agent of the present embodiment may be a microcapsule-based gas generating agent.

In the present embodiment, a microcapsule-based gas generating agent refers to a gas generating agent having a core-shell structure.

A specific example of the microcapsule-based gas generating agent is a microcapsule-based gas generating agent having as a core component an oxalic acid salt of an aminoguanidine compound or a composition containing the oxalic acid salt of the aminoguanidine compound and further the adjuvant and the like. The main component of the shell of the microcapsule-based gas generating agent is not particularly limited, and an example is polymethyl methacrylate, and a fatty acid salt or a surfactant as a dispersant which will be described below is preferably contained. Introducing air bubbles into a rubber or a thermoplastic resin using such a microcapsule-based gas generating agent makes it possible to introduce uniform air bubbles into a polymer without inhibiting vulcanization and crosslinking and, moreover, without generating degradation residues and VOC components, thereby a decrease in crosslinking density is suppressed, and a crosslinked foam having a good air bubble state and excellent foam characteristics can be obtained.

Although the polymethyl methacrylate is preferably a homopolymer having a methyl methacrylate monomer as a constitutional unit, it may be copolymerized with another monomer as long as the effect of the present invention is not impaired. Another monomer is not particularly limited, and examples include acrylic acid esters such as methyl acrylate, ethyl acrylate, butyl acrylate, and dicyclopentenyl acrylate, methacrylic acid esters such as ethyl methacrylate, butyl methacrylate, and isobornyl methacrylate, acrylonitrile, methacrylonitrile, vinylidene chloride, vinyl chloride, styrene, vinyl acetate, α-methylstyrene, chloroprene, neoprene, and butadiene.

The crosslinking agent (D) used when producing the microcapsule-based gas generating agent is not particularly limited, and examples include (poly)ethylene glycol, divinylbenzene, ethylene glycol di(meth)acrylate, triethylene glycol di(meth)acrylate, allyl methacrylate, triallyl isocyanate, triacrylformal, trimethylolpropane tri(meth)acrylate, 1,3-butylglycol dimethacrylate, and pentaerythritol tri(meth)acrylate. In particular, ethylene glycol dimethacrylate, (poly)ethylene glycol, and trimethylolpropane tri(meth)acrylate are preferable.

A preferable range of the proportion of the crosslinking agent (D) added is 1 to 5 mass % based on the mass of the microcapsule shell monomers (the total mass of the methyl methacrylate monomer and other monomers). When the proportion of the crosslinking agent (D) is less than 1 mass %, the crosslinking of the capsule shell is insufficient, degradation residues generated when the core component degrades cannot be efficiently adsorbed, and therefore degradation residues readily pass through the capsule shell. When the proportion of the crosslinking agent (D) exceeds 5 mass %, the capsule shell becomes hard and brittle, the capsule shell breaks during the degradation of the core component, and the effect of adsorbing degradation residues is decreased.

A polymerization initiator used when producing the microcapsule-based gas generating agent is not particularly limited, and those that are commonly used in this field can be used. Examples of polymerization initiators that can be used include dialkyl peroxides, diacyl peroxides, peroxy esters, peroxydicarbonates, and azo compounds. Specific examples include dialkyl peroxides such as methylethyl peroxide, di-t-butyl peroxide, and dicumyl peroxide, diacyl peroxides such as isobutyl peroxide, benzoyl peroxide, 2,4-dichlorobenzoyl peroxide, and 3,5,5-trimethylhexanoyl peroxide, peroxy esters such as t-butyl peroxypivalate, t-hexyl peroxypivalate, t-butyl peroxyneodecanoate, t-hexyl peroxyneodecanoate, 1-cyclohexyl-1-methylethyl peroxyneodecanoate, 1,1,3,3-tetramethylbutyl peroxyneodecanoate, cumyl peroxyneodecanoate, and (α,α-bis-neodecanoylperoxy) diisopropylbenzene, peroxydicarbonates such as bis(4-t-butylcyclohexyl) peroxydicarbonate, di-n-propyl-peroxydicarbonate, di-isopropyl peroxydicarbonate, and di-(3-methyl-3-methoxybutyl) peroxydicarbonate, persulfuric acid salts such as potassium persulfate and ammonium persulfate, and azo compounds such as 2,2'-azobisisobutyronitrile, 2,2'-azobis(2,4-dimethylvaleronitrile), 2,2'-azobis(4-methoxy-2,4-dimethylvaleronitrile), and 1,1'-azobis(1-cyclohexanecarbonitrile).

The microcapsule-based gas generating agent can be produced by an emulsion polymerization method such as a suspension polymerization method. For example, a solid-phase (S phase) core component (for example, an oxalic acid salt of an aminoguanidine compound or a composition containing the oxalic acid salt of the aminoguanidine compound and further the adjuvant and the like) is added to an oil phase (O phase) having a monomer (for example, a methyl methacrylate monomer) for a microcapsule shell, a crosslinking agent (D), and a polymerization initiator, and stirring/mixing is performed to thereby prepare a S/O emulsion. This S/O emulsion is added to a water phase (W phase)

and stirred/mixed to thereby prepare a S/O/W suspension. This S/O/W suspension is introduced into a pressure polymerizer such as an autoclave and subjected to pressure polymerization to obtain a cake-like substance. This cake-like substance is filtered off by a commonly used method such as filtration or centrifugation, the resulting residue is washed with distilled water about 3 to 5 times, and then dried at a temperature of 40 to 60° C. all day and night using a dryer, and it is thus possible to obtain the microcapsule-based gas generating agent. As for pressure polymerization conditions, commonly used conditions can be used, and, for example, the polymerization temperature is 40 to 70° C., the polymerization time is 10 to 24 hours, and the polymerization pressure is 0.2 to 0.3 MPa.

Suspension polymerization is preferably performed in the presence of a dispersion stabilizer and a dispersion stability aid. The dispersion stabilizer is not particularly limited, and, for example, silica, calcium phosphate, magnesium hydroxide, aluminum hydroxide, ferric hydroxide, barium sulfate, calcium sulfate, sodium sulfate, sodium chloride, calcium oxalate, calcium carbonate, barium carbonate, and magnesium carbonate can be used. In particular, silica and calcium phosphate are preferable.

The dispersion stability aid is not particularly limited, and, for example, a condensate of diethanolamine and aliphatic dicarboxylic acid, a condensate of urea and formaldehyde, polyvinylpyrrolidone, polyethylene oxide, polyethyleneimine, tetramethylammonium hydroxide, gelatin, methylcellulose, polyvinyl alcohol, dioctyl sulfosuccinate, polyglycerin fatty acid ester, and sorbitan ester can be used.

A preferable combination of a dispersion stabilizer and a dispersion stability aid is a combination of colloidal silica and a condensate. The condensate is preferably a condensate of diethanolamine and aliphatic dicarboxylic acid, and, in particular, a condensate of diethanolamine and adipic acid and a condensate of diethanolamine and itaconic acid are preferable. A condensate is specified by the acid value, and an acid value of 65 or more and 90 or less is preferable. Moreover, the addition of an inorganic salt, in particular, sodium chloride, sodium sulfate, or the like is suitable for obtaining a uniform microcapsule-based gas generating agent having a small particle diameter.

The microcapsule-based gas generating agent preferably contains a fatty acid salt or a surfactant as a dispersant. This fatty acid salt or surfactant is added to the oil phase (O phase) having a monomer for the microcapsule shell, a crosslinking agent (D), and a polymerization initiator when producing the microcapsule-based gas generating agent. The content of the fatty acid salt or surfactant in the microcapsule-based gas generating agent is preferably 0.01 to 3 mass % based on the core component (the compound represented by general formula (1) or a composition containing the compound represented by general formula (1) and further the adjuvant and the like). When the content is 0.01 mass % or more, there is a tendency that the core component is sufficiently stable, thus the coagulation of solid phase/oil phase droplets is suppressed, and aggregates are unlikely to be formed during polymerization. When the content is 3 mass % or less, there is a tendency that the viscosity of solid phase/oil phase droplets does not become excessively high, droplets are unlikely to adhere to each other, and a broadening of the particle size distribution of microcapsule particles is suppressed.

The fatty acid salt is not particularly limited, and examples include fatty acid amides such as stearic acid amide and arachidic acid amide, zinc stearate, calcium stearate, potassium stearate, aluminum stearate, lithium stearate, sodium stearate, magnesium stearate, zinc palmitate, zinc myristate, calcium palmitate, and sodium palmitate. Among these fatty acid salts, one or more selected from higher fatty acid salts having 15 to 22 carbon atoms are preferable, and one or more higher fatty acid salts of metals selected from the group consisting of potassium, calcium, lithium, and magnesium are more preferable. Titanium oxide, zinc oxide, talc, calcium carbonate, and the like may be used as long as the effect of the present invention is not impaired.

The surfactant is not particularly limited, and includes known cationic surfactants, anionic surfactants, ampholytic surfactants, and nonionic surfactants. Cationic surfactants are not particularly limited, and examples include alkyltrimethylammonium salts, dialkyldimethylammonium salts, and alkyldimethylbenzylammonium salts. Anionic surfactants are not particularly limited, and examples include sulfonate-type anionic surfactants such as alkylbenzenesulfonates, alkylsulfosuccinates, and allylsulfonates, sulfate-type anionic surfactants such as alkylsulfates and polyoxyethyleneakylsulfates, and lignosulfites.

Nonionic surfactants are not particularly limited, and examples include sugar ester-type nonionic surfactants such as sorbitan fatty acid esters and polyoxyethylene sorbitan fatty acid esters, fatty acid ester-type nonionic surfactants such as polyoxyethylene fatty acid esters, vegetable oil-type nonionic surfactants such as polyoxyethylene castor oil, alcohol-type nonionic surfactants such as polyoxyethylene alkyl ethers, alkylphenol-type nonionic surfactants such as polyoxyethylene alkyl (C8-12) phenyl ether-formalin condensates, polyoxyethylene-polyoxypropylene block polymer-type nonionic surfactants such as polyoxyethylene-polyoxypropylene block polymers, and polyaromatic-type nonionic surfactants such as phenyl phenyl ether.

Among the surfactants, nonionic surfactants are most suitable. It is also possible to use anionic surfactants, cationic surfactants, and various additives in combination as long as the effect of the present invention is not impaired.

A preferable range of the HLB value (Hydrophile-Lipophile Balance) of the surfactants is 0.01 to 16, more preferably 0.01 to 9, and even more preferably 0.01 to 3. When the HLB value exceeds 16, the surfactants have strong hydrophilicity, and the solid phase in solid phase/oil phase droplets has an affinity for the aqueous phase. When the solid phase of solid phase/oil phase droplets has an affinity for the aqueous phase, the core component is concentrated near the surface of polymerized microcapsule particles, and the effect of reducing degradation residues is small when the core component degrades. When the HLB value is 16 or less, the solid phase in solid phase/oil phase droplets is uniformly dispersed in the oil phase, and thus the effect of reducing degradation residues is large. In particular, when the HLB value is 3 or less, the surfactants are highly lipophilic, the solid phase in solid phase/oil phase droplets is concentrated in the center of the oil phase, a microcapsule-based gas generating agent in which the core component is concentrated in the center of particles after polymerization is obtained, and also the effect of reducing degradation residues during heating is large.

The foamable composition of the present embodiment comprises the above-described gas generating agent and a material to be foamed.

In the foamable composition of the present embodiment, the material to be foamed that is contained together with the above-described gas generating agent is not particularly limited, and examples include thermoplastic resins and/or rubbers. One material to be foamed may be used singly, or two or more may be used in combination. Examples of the thermoplastic resins include, but are not limited to, vinyl chloride resins, vinyl chloride copolymer resins, polyethylene, polypropylene, and polyolefin copolymer resins represented by ethylene-propylene copolymers, polystyrene resins, and acrylonitrile-butadiene-styrene copolymers (ABS resins).

The foamable composition of the present embodiment may further comprise a crosslinking agent (E). The crosslinking agent (E) contained in the foamable composition of the present embodiment may be the same as or different from the crosslinking agent (C) contained in the above-described gas generating agent.

The foam of the present embodiment is a foam obtained by foaming the above-described foamable composition.

A method for producing the foam of the present embodiment is not particularly limited as long as the method comprises a step of heating a foamable composition comprising the above-described gas generating agent and a material to be foamed, and a commonly used method for producing a foam can be used. For example, a foamable composition (an unfoamed resin composition) can be prepared by kneading a thermoplastic resin, a crosslinking agent (E), and the above-described gas generating agent with heated kneading rolls. The kneading temperature is preferably 90 to 130° C. Here, the crosslinking agent (E) contained in the foamable composition is not particularly limited, and examples include dicumyl peroxide, di-t-butyl peroxide, 2,5-dimethyl-2,5-di-(t-butylperoxy)hexane, 2,5-dimethyl-2,5-di-(t-butylperoxy)hexyne, 1,3-bis(t-butylperoxyisopropyl)benzene, 1,1-bis(t-butylperoxy)-3,3,5-trimethylcyclohexane, 1,1-bis[t-butylperoxy]cyclohexane, n-butyl-4,4-bis(t-butylperoxy)valerate, benzoyl peroxide, p-chlorobenzoyl peroxide, 2,4-dichlorobenzoyl peroxide, t-butyl peroxybenzoate, t-butyl perbenzoate, t-butylperoxy isopropyl carbonate, diacetyl peroxide, lauroyl peroxide, and t-butyl cumyl peroxide. One crosslinking agent (E) may be used singly, or two or more may be used in combination. The content of crosslinking agent (E) is preferably 0.1 to 10 parts by mass and more preferably 0.5 to 1.5 parts by mass based on 100 parts by mass of the thermoplastic resin.

The unfoamed resin composition thus obtained is introduced into a metal mold, pressurized with a press, and thereby a foam of a resin composition (for example, a thermoplastic resin) is obtained. The metal mold thickness, pressurizing conditions, and the like are not particularly limited, and a conventionally known foam molding method can be suitably employed according to the kind, the application, and the like of the thermoplastic resin. For example, the unfoamed resin composition is introduced into a metal mold having a thickness of 1 to 30 mm to an extent of 100%, pressurized with a press for 3 to 60 minutes under 100 to 170° C. and 150 kg/cm$^2$ conditions, and water-cooled for 3 to 60 minutes, and thereby a sheet-like composition is obtained. The resulting sheet-like composition is left to stand still for one day, then heated for 1 hour in an oven at 40 to 80° C., and heated at 130 to 250° C. for 150 to 600 seconds, and a foam of the resin composition is obtained.

When producing a foam of the resin composition in this way, the amount of the above-described gas generating agent used can be suitably selected according to the intended expansion ratio and is not particularly limited, but preferably 1 to 30 parts by mass of the gas generating agent is blended based on 100 parts by mass of a synthetic resin material.

Examples of rubbers used in the present embodiment include, but are not limited to, natural rubber (NR), polyisoprene rubber, styrene-butadiene rubber (SBR), acrylonitrile-butadiene rubber, chloroprene rubber, ethylene-propylene rubber, ethylene-propylene-diene rubber, and butadiene rubber.

As a method in which the above-described gas generating agent is blended with a rubber to prepare a foamable composition and a foam is produced therefrom, commonly used foam production conditions can be used. For example, a rubber material, a vulcanizing agent, a filler, a vulcanization accelerator, and the above-described gas generating agent are uniformly dispersed with kneading rolls to obtain a foamable composition. The resulting foamable composition is fed to an extruder heated to 70 to 90° C. to prepare an unvulcanized molding. The resulting unvulcanized molding is heated for 5 to 15 minutes in an oven heated to 60 to 220° C. to perform vulcanization and foaming, and a foam of the rubber material is obtained.

Although the proportion of each component blended in the foamable composition is not particularly limited, preferably 0.1 to 10 parts by mass of the vulcanizing agent is blended based on 100 parts by mass of the rubber material. Preferably 10 to 150 parts by mass of the filler is blended based on 100 parts by mass of the rubber material. Preferably 0.1 to 20 parts by mass of the vulcanization accelerator is blended based on 100 parts by mass of the rubber material.

When producing a foam of the rubber material in this way, the amount of the above-described gas generating agent used can be suitably selected according to the intended expansion ratio and is not particularly limited, but preferably 1 to 20 parts by mass of the gas generating agent is blended based on 100 parts by mass of the rubber.

Specific examples of the vulcanizing agent used in the present embodiment are not particularly limited, and an example is sulfur.

Specific examples of the filler used in the present embodiment are not particularly limited, and examples include heavy and light calcium carbonates, and carbon black.

Specific examples of the vulcanization accelerator used in the present embodiment are not particularly limited, and examples include dithiocarbamic acid salt-based vulcanization accelerators and dithiocarbamic acid-based vulcanization accelerators, and specifically examples include DM (dibenzylthiazole disulfide), zinc dimethyldithiocarbamate, and zinc dibutyldithiocarbamate.

The foamable composition of the present embodiment may contain other additives. Other additives are not particularly limited, and examples include Diana Process Oil, zinc oxide, stearic acid, calcium oxide, urea-based auxiliaries, silicon dioxide (silica), talc, magnesium oxide, zinc stearate, calcium hydroxide, barium stearate, dibasic lead phosphite, and lead oxide.

EXAMPLES

The present invention is described in more detail by way of Examples and Comparative Examples below, but the present invention is not at all limited to the Examples. In Examples and Comparative Examples provided below, unless specified otherwise, the structure of a compound used for a gas generating agent was identified by CHN elemental analysis and the melting point, and the degradation starting temperature of a gas generating agent, the amount of generated gas, and the amount of generated ammonia were respectively evaluated by the following methods.

<Measurement of Degradation Starting Temperature of Gas Generating Agent>

The degradation starting temperature of a gas generating agent was measured using a differential thermal-thermogravimetric simultaneous analyzer (EXSTAR 6000 manufactured by SII NanoTechnology Inc.) in air under conditions where the starting temperature was 25° C. and the temperature was increased at 10° C./min. The temperature at which the weight was lower by 5% than the weight at the beginning of increasing the temperature was regarded as the degradation starting temperature.

<Measurement of Amount of Generated Gas>

After 0.5 g of a gas generating agent was placed in a test tube and 10 mL of liquid paraffin as a heating medium was added, the test tube and a gas buret were connected by a rubber tube, and the test tube was immersed in an oil bath at 60° C. Then, the oil bath was heated to 240° C. at a heating rate of 2° C./min. Gas generated during this heating was all captured by the gas buret to determine the amount (mL) of generated gas per gram of the gas generating agent.

<Measurement of Amount of Generated Ammonia>

After 0.5 g of a gas generating agent was placed in a test tube and 10 mL of liquid paraffin was added as a heating medium, this test tube, a screw-cap test tube, and a screw-cap bottle having 100 mL of 0.1 N hydrochloric acid were connected by a rubber tube in this order. While allowing nitrogen gas to flow at a flow rate of 0.4 L/min, the test tube containing the gas generating agent was heated to 228° C. in a block heater. Ammonia gas generated during this heating was captured by 0.1 N hydrochloric acid, and ammonium ions in hydrochloric acid were quantified by an ion chromatograph (DX-320J manufactured by Nippon Dionex K.K.) to determine the amount (mg) of generated ammonia gas per gram of the gas generating agent.

(Synthesis Example 1) Synthesis of Aminoguanidine Oxalate (2)

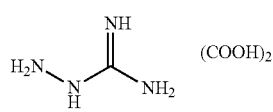

To a 50 mL recovery flask were added 3.98 g (29 mmol) of aminoguanidine carbonate (manufactured by Tokyo Chemical Industry Co., Ltd.) and 18 g of water, and then the mixture was stirred using a magnetic stirrer. Then, 2.63 g (29 mmol) of oxalic acid was added in small portions, and stirring was performed until foaming settled. Precipitated white solids were collected by filtration, washed with methanol, and then vacuum-dried at 50° C. for 18 hours, thus giving 3.39 g (21 mmol) of white solids. Elemental analysis was performed on the resulting solids using a carbon-hydrogen-nitrogen simultaneous quantifier CHN Coder MT-6 (Yanaco Analytical Instruments Inc.), the values calculated were C, 21.96; H, 4.91; N, 34.14 and, on the other hand, the values found were C, 21.78; H, 4.75; N, 34.22, and the resulting solids were thus confirmed as aminoguanidine oxalate. The molar yield was 71%. The melting point of the resulting solids measured using a micro melting point apparatus BY-1 (manufactured by Yazawa Scientific Co., Ltd.) was 211 to 212° C.

(Comparative Synthesis Example 1) Synthesis of Guanidine Oxalate (3)

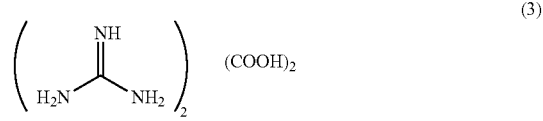

To a 30 mL recovery flask were added 1.80 g (10 mmol) of guanidine carbonate (manufactured by Tokyo Chemical Industry Co., Ltd.) and 2.5 mL of water and the mixture was stirred at room temperature, and then 907 mg (10 mmol) of oxalic acid (manufactured by Wako Pure Chemical Industries, Ltd.) was added. Foaming occurred when oxalic acid was added. Further, after 3 hours of stirring, the reaction solution was added dropwise to ethanol, precipitated white solids were collected by filtration, washed with ethanol, and then vacuum-dried at 50° C. for 17 hours, thus giving 1.55 g (7.5 mmol) of white solids. When elemental analysis was performed on the resulting solids using a carbon-hydrogen-nitrogen simultaneous quantifier CHN Coder MT-6 (Yanaco Analytical Instruments Inc.), the values calculated were C, 23.08; H, 5.81; N, 40.37 and, on the other hand, the values found were C, 23.05; H, 6.22; N, 39.92, and the resulting solids were thus confirmed as guanidine oxalate. The molar yield was 75%. The melting point of the resulting solids measured using a micro melting point apparatus BY-1 (manufactured by Yazawa Scientific Co., Ltd.) was 149 to 150° C.

Example 1

The degradation starting temperature of aminoguanidine oxalate (2) obtained in Synthesis Example 1 and the amount of generated gas were measured. The degradation starting temperature and the amount of generated gas are shown in Table 1.

Comparative Example 1

The degradation starting temperature of guanidine oxalate (3) obtained in Comparative Synthesis Example 1 and the amount of generated gas were measured under the same conditions as in Example 1. The degradation starting temperature and the amount of generated gas are shown in Table 1.

Comparative Example 2

The degradation starting temperature of guanidine carbonate (manufactured by Tokyo Chemical Industry Co., Ltd.) and the amount of generated gas were measured under the same conditions as in Example 1. The degradation starting temperature and the amount of generated gas are shown in Table 1.

Comparative Example 3

The degradation starting temperature of guanidine nitrate (manufactured by Tokyo Chemical Industry Co., Ltd.) and the amount of generated gas were measured under the same conditions as in Example 1. The degradation starting temperature and the amount of generated gas are shown in Table 1.

Comparative Example 4

The degradation starting temperature of aminoguanidine carbonate (manufactured by Tokyo Chemical Industry Co., Ltd.) and the amount of generated gas were measured under the same conditions as in Example 1. The degradation starting temperature and the amount of generated gas are shown in Table 1.

Comparative Example 5

The degradation starting temperature of aminoguanidine nitrate (manufactured by SIGMA-ALDRICH) and the amount of generated gas were measured under the same conditions as in Example 1. The degradation starting temperature and the amount of generated gas are shown in Table 1.

Comparative Example 6

The degradation starting temperature of 4,4'-oxybis(benzenesulfonyl hydrazide) (OBSH) (manufactured by Eiwa Chemical Ind. Co., Ltd.) and the amount of generated gas were measured under the same conditions as in Example 1. The degradation starting temperature and the amount of generated gas are shown in Table 1.

TABLE 1

| | Example 1 | Comparative Example 1 | Comparative Example 2 | Comparative Example 3 | Comparative Example 4 | Comparative Example 5 | Comparative Example 6 |
|---|---|---|---|---|---|---|---|
| Degradation starting temperature (°C.) | 193 | 205 | 186 | 294 | 106 | 258 | 173 |
| Amount of generated gas (mL/g) | 160 | 3 | 38 | 2 | 144 | 0 | 120 |

It was found from Table 1 that due to the formation of a salt with oxalic acid, aminoguanidine and the like generate an increased amount of gas, or have a degradation starting temperature of 120° C. or higher and become capable of coping with the molding temperature of general-purpose plastics (for example, thermoplastic resins) and rubbers.

Example 2

The amount of generated ammonia gas of aminoguanidine oxalate (2) obtained in Synthesis Example 1 (the compound represented by formula (2)) was measured by the method described above except that the heating temperature of the block heater was changed to 185° C. The result is shown in Table 2.

Comparative Example 7

The amount of generated ammonia gas of guanidine oxalate (3) obtained in Comparative Synthesis Example 1 (the compound represented by formula (3)) was measured under the same conditions as above. The result is shown in Table 2.

Comparative Example 8

The amount of generated ammonia gas of azodicarbonamide (ADCA) (manufactured by Eiwa Chemical Ind. Co., Ltd.) was measured under the same conditions as above except that the heating temperature of the block heater was changed to 210° C. The result is shown in Table 2.

TABLE 2

| | Example 2 | Comparative Example 7 | Comparative Example 8 |
|---|---|---|---|
| Amount of generated ammonia gas (mg/g) | 0.04 | 1.46 | 11.11 |

It was found from Table 2 that the gas generating agents of the present embodiment generate smaller amounts of ammonia gas and, as chemical blowing agents for general-purpose plastics (for example, thermoplastic resins) and rubbers, do not contaminate the metal mold during molding and are highly safe.

Example 3

Polyethylene (trade name "LE200M" manufactured by Japan Polyethylene Corporation) in an amount of 100 parts by mass was kneaded with an open mill heated to 120° C., then 16 parts by mass of aminoguanidine oxalate (2) obtained in Synthesis Example 1 (the compound represented by formula (2)) was added and kneaded for 4 minutes and 30 seconds, then 0.8 parts by mass of dicumyl peroxide (DCP) (trade name "Percumyl D" manufactured by NOF Corporation) was added and kneaded for 1 minute and 30 seconds, and the kneaded material was removed from the open mill. The kneaded material was introduced into a metal mold (2 mm) of a press heated to 165° C. such that the inner volume was filled 100%, pressurized for 3 minutes at a pressing pressure of 50 kg/cm$^2$, then pressurized for 3 minutes at a pressing pressure of 150 kg/cm$^2$, and water-cooled for 5 minutes, thus giving a sheet-like composition. The resulting sheet-like composition was left to stand still for one day, heated for 1 hour in an oven at 60° C., and heated at 220° C. for 244 seconds, thus giving a foam. The evaluation results of the resulting foam are shown in Table 3.

Example 4

A foam was obtained under the same conditions as in Example 3 except that the amount of aminoguanidine oxalate (2) obtained in Synthesis Example 1 (the compound represented by formula (2)) added was changed to 23 parts by mass, and the time of heating at 220° C. was 244 seconds. The evaluation results of the resulting foam are shown in Table 3.

Example 5

A foam was obtained under the same conditions as in Example 3 except that the amount of aminoguanidine oxalate (2) obtained in Synthesis Example 1 (the compound represented by formula (2)) added was changed to 23 parts by mass, the amount of DCP added was changed to 1.5 parts by mass, and the time of heating at 220° C. was 261 seconds. The evaluation results of the resulting foam are shown in Table 3.

Example 6

A foam was obtained under the same conditions as in Example 3 except that the amount of aminoguanidine oxalate (2) obtained in Synthesis Example 1 (the compound represented by formula (2)) added was changed to 23 parts by mass, the amount of DCP added was changed to 0.3 parts by mass, and the time of heating at 220° C. was 268 seconds. The evaluation results of the resulting foam are shown in Table 3.

Example 7

A foam was obtained under the same conditions as in Example 3 except that the amount of aminoguanidine oxalate (2) obtained in Synthesis Example 1 (the compound represented by formula (2)) added was changed to 23 parts by mass, DCP was changed to 2.0 parts by mass of 1,1-bis[t-butylperoxy]cyclohexane (trade name "Perhexa C-40" manufactured by NOF Corporation), and the time of heating at 220° C. was 250 seconds. The evaluation results of the resulting foam are shown in Table 3.

Example 8

A foam was obtained under the same conditions as in Example 3 except that the amount of aminoguanidine oxalate (2) obtained in Synthesis Example 1 (the compound represented by formula (2)) added was changed to 23 parts by mass, DCP was changed to 0.8 parts by mass of di-(2-t-butylperoxyisopropyl)benzene (trade name "Perbutyl P" manufactured by NOF Corporation), and the time of heating at 220° C. was 240 seconds. The evaluation results of the resulting foam are shown in Table 3.

Comparative Example 9

A foam was obtained under the same conditions as in Example 3 except that the gas generating agent was changed to azodicarbonamide (ADCA) (manufactured by Eiwa Chemical Ind. Co., Ltd.), and the time of heating at 220° C. was 305 seconds. The evaluation results of the resulting foam are shown in Table 3.

Comparative Example 10

A foam was obtained under the same conditions as in Example 3 except that the gas generating agent was changed to sodium hydrogencarbonate (trade name "Cellborn FE-507", manufactured by Eiwa Chemical Ind. Co., Ltd.) and the time of heating at 220° C. was 240 seconds. The evaluation results of the resulting foam are shown in Table 3.

TABLE 3

| | | Example 3 | Example 4 | Example 5 | Example 6 | Example 7 | Example 8 | Comparative Example 9 | Comparative Example 10 |
|---|---|---|---|---|---|---|---|---|---|
| Resin | Polyethylene | 100 parts | 100 parts | 100 parts | 100 parts | 100 parts | 100 parts | 100 parts | 100 parts |
| Gas generating agent | ADCA | — | — | — | — | — | — | 16 parts | — |
| | Cellborn FE-507 | — | — | — | — | — | — | — | 16 parts |
| | Formula (2) | 16 parts | 23 parts | 23 parts | 23 parts | 23 parts | 23 parts | — | — |
| Crosslinking agent (E) | Percumyl D | 0.8 parts | 0.8 parts | 1.5 parts | 0.3 parts | — | — | 0.8 parts | 0.8 parts |
| | Perhexa C-40 | — | — | — | — | 2.0 parts | — | — | — |
| | Perbutyl P | — | — | — | — | — | 0.8 parts | — | — |
| Foaming time [sec] | | 200 | 244 | 261 | 268 | 250 | 240 | 305 | 240 |
| Specific gravity [g/cm$^3$] | | 0.200 | 0.218 | 0.167 | 0.102 | 0.162 | 0.202 | 0.032 | 0.318 |
| Expansion ratio | | 4.6 | 4.2 | 5.5 | 9.0 | 5.7 | 4.6 | 28.8 | 2.9 |
| Number of air bubbles n = 5 per 1 cm | | 42-46 | 39-42 | 40-44 | 34-40 | 27-40 | 32-37 | 23-30 | 7-11 |
| Color of foam | | White | White | White | White | White | White | Pale yellow | White |

In the present Examples, the specific gravity, the expansion ratio, and the number of air bubbles of a foam were measured as follows.
Specific gravity: measured with an electronic gravimeter MD-200S.
Expansion ratio: calculated by the specific gravity of polyethylene (0.92 g/cm$^3$)/the specific gravity of a foam.
Number of air bubbles: measured with a microscope HIROX KH7700 2D measurement.
It was found from Table 3 that white foams are obtained by using the gas generating agents of the present invention.

Example 9

Saturated hydrocarbon rubber (trade name "EPT 4021" manufactured by Mitsui Chemicals, Inc.) in an amount of 100 parts by mass was kneaded with a cooled (water-flowed) roll mill, then 70 parts by mass of carbon black (trade name "Asahi #50 UG" manufactured by Asahi Carbon Co., Ltd.), 40 parts by mass of light calcium carbonate (manufactured by Ohmi Chemical Industry Co., Ltd.), 45 parts by mass Diana Process Oil (trade name "PW-90", manufactured by Idemitsu Kosan Co., Ltd.), 5 parts by mass of zinc oxide (ZnO (zinc white) manufactured by Mitsui Mining & Smelting Co., Ltd.), and 1 part by mass of stearic acid ($CH_3(CH_2)_{16}COOH$, trade name "Tsubaki" manufactured by NOF Corporation) were added and kneaded, thus giving kneaded material A. Kneaded material A was stored for 1 day or more at normal temperature for aging. The aged kneaded material A was kneaded with a cooled (water-flowed) roll mill, then 1.1 parts by mass of a dithiocarbamic acid salt-based vulcanization accelerator (zinc dimethyldithiocarbamate, trade name "Nocceler PZ" manufactured by Ouchi Shinko Chemical Industrial Co., Ltd.) and 1.7 parts by mass of a dithiocarbamic acid-based vulcanization accelerator (zinc dibutyldithiocarbamate, trade name "Nocceler BZ" manufactured by Ouchi Shinko Chemical Industrial Co., Ltd.) were added and kneaded, then 1.7 parts by mass of sulfur (trade name "Fine Powder Sulfur S" manufactured by Hosoi Chemical Industry Co., Ltd.), 5 parts by mass of calcium oxide (trade name "F Lime 1300D" manufactured by Calfine Co., Ltd.), 5.25 parts by mass of aminoguanidine oxalate (2) obtained in Synthesis Example 1 (the compound represented by formula (2)), and 6 parts by mass of a urea-based auxiliary (trade name "Cellpaste K5" manufactured by Eiwa Chemical Ind. Co., Ltd.) were added and kneaded, and kneaded material B was removed from the roll mill. Kneaded material B was introduced into an extruder and extruded at a die temperature of 50° C., thus giving a sheet-like molding. The resulting sheet-like molding was aged for 1 day at normal temperature and then heated for 10 minutes in an oven at 180° C., thus giving a form. The expansion ratio of the resulting blowing agent was 1.280. As a blank for calculating the expansion ratio, kneaded material C was produced by the same production method as that for kneaded material B except that no aminoguanidine oxalate (2) was blended, and the specific gravity of kneaded material C was measured. The expansion ratio was calculated by the specific gravity of kneaded material C (0.860 g/cm³)/the specific gravity of the foam (0.672 g/cm³). The specific gravity was measured with an electronic gravimeter MD-200S.

The invention claimed is:

1. A foamable composition comprising:
   a gas generating agent including an oxalic acid salt of an aminoguanidine compound represented by general formula (1) below

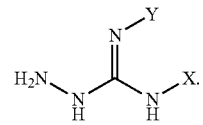

wherein X and Y are each independently a hydrogen atom or an amino group; and
   a material to be foamed.

2. The foamable composition according to claim 1, wherein in the oxalic acid salt of the aminoguanidine compound, a molar ratio of the aminoguanidine compound to oxalic acid (aminoguanidine compound:oxalic acid) is in a range of 1:1 to 2:1.

3. The foamable composition according to claim 1, wherein the aminoguanidine compound is aminoguanidine.

4. The foamable composition according to claim 1, wherein the gas generating agent is a microcapsule-based agent.

5. The foamable composition according to claim 1, wherein the material to be foamed is a thermoplastic resin and/or a rubber.

6. A method for producing a foam, comprising a step of heating the foamable composition according to claim 1.

7. A foam, wherein the foam is obtained by foaming the foamable composition according to claim 1.

* * * * *